United States Patent
Corrales et al.

(10) Patent No.: US 10,695,331 B2
(45) Date of Patent: Jun. 30, 2020

(54) VETERINARY COMPOSITION COMPRISING IMIDACLOPRID, MOXIDECTIN AND PRAZIQUANTEL FOR CUTANEOUS TOPICAL APPLICATION (SPOT ON), FOR THE TREATMENT AND PREVENTION OF ECTO AND ENDOPARASITOSES AFFECTING DOGS

(71) Applicant: LABYES USA, LLC, Milford, Kent County, DE (US)

(72) Inventors: Carlos D. Corrales, Buenos Aires República (AR); Jorge A. Dale, CABA República (AR)

(73) Assignee: LABYES USA, LLC, Milford, DE (US)

( * ) Notice: Subject to any disclaimer, the term of this patent is extended or adjusted under 35 U.S.C. 154(b) by 0 days.

(21) Appl. No.: 16/074,696

(22) PCT Filed: May 16, 2017

(86) PCT No.: PCT/US2017/032851
§ 371 (c)(1),
(2) Date: Aug. 1, 2018

(87) PCT Pub. No.: WO2017/201010
PCT Pub. Date: Nov. 23, 2017

(65) Prior Publication Data
US 2019/0070158 A1    Mar. 7, 2019

(30) Foreign Application Priority Data
May 18, 2016   (AR) .............................. 20160101448

(51) Int. Cl.
| | |
|---|---|
| A61K 31/4439 | (2006.01) |
| A61K 9/00 | (2006.01) |
| A61K 47/18 | (2017.01) |
| A61K 47/20 | (2006.01) |
| A61P 33/14 | (2006.01) |
| A61K 31/365 | (2006.01) |
| A61K 31/4985 | (2006.01) |
| A61K 47/10 | (2017.01) |
| A61K 47/14 | (2017.01) |

(52) U.S. Cl.
CPC ........ *A61K 31/4439* (2013.01); *A61K 9/0017* (2013.01); *A61K 31/365* (2013.01); *A61K 31/4985* (2013.01); *A61K 47/10* (2013.01); *A61K 47/14* (2013.01); *A61K 47/18* (2013.01); *A61K 47/20* (2013.01); *A61P 33/14* (2018.01)

(58) Field of Classification Search
CPC .............. A61K 2300/00; A61K 31/365; A61K 31/4439; A61K 31/4985; A61K 47/10; A61K 47/14; A61K 47/18; A61K 47/20; A61K 9/0017; A61P 33/14
See application file for complete search history.

(56) References Cited

U.S. PATENT DOCUMENTS

| | | | |
|---|---|---|---|
| 9,237,751 B2 * | 1/2016 | Reynolds | ............... A01N 43/60 |
| 2004/0198676 A1 * | 10/2004 | Soll | ...................... A61K 9/0017 |
| | | | 514/28 |
| 2009/0017024 A1 | 1/2009 | Estok et al. | |
| 2009/0036458 A1 * | 2/2009 | Fattohi | ................... A61K 31/05 |
| | | | 514/250 |
| 2011/0160218 A1 | 6/2011 | Holmes et al. | |
| 2012/0071484 A1 * | 3/2012 | Reynolds | ............... A01N 43/60 |
| | | | 514/250 |
| 2013/0225516 A1 | 8/2013 | Soll et al. | |

OTHER PUBLICATIONS

Hutchinson et al. (Veterinary Record, 2001, 148, 695-696). (Year: 2001).*
International Search Report dated Jul. 14, 2017 dated Aug. 10, 2017.

* cited by examiner

*Primary Examiner* — Umamaheswari Ramachandran
(74) *Attorney, Agent, or Firm* — Norris McLaughlin, P.A.

(57) ABSTRACT

A monodose veterinary composition for topical application (spot on) for canines, the said composition comprising: (a) Imidacloprid, between 8.18 and 10.00%, (b) Moxidectin, between 2.86 and 3.50%, (c) Praziquantel, between 8.18 and 10.00%, and (d) an aprotic solvent selected from Dimethyl sulfoxide (DMSO), N,N-dimethylacetamide (DMAC), N,N-dimethylformamide (DMF) and their mixtures, between 65.45 and 80.00%; together with excipients acceptable from the veterinary viewpoint, where the percentages are related to the composition's total weight. The use of an effective amount of (a) Imidacloprid, (b) Moxidectin; (c) Praziquantel; and (d) an aprotic solvent selected from Dimethyl sulfoxide (DMSO), N,N-dimethylacetamide (DMAC), N,N-dimethylformamide (DMF) and mixtures of these, together with veterinary acceptable excipients, for the preparation of a monodose veterinary composition for the treatment, control and prevention of ecto and endoparasitoses in canines, where the said veterinary composition is adapted to be administered topically (spot on).

6 Claims, No Drawings

VETERINARY COMPOSITION COMPRISING IMIDACLOPRID, MOXIDECTIN AND PRAZIQUANTEL FOR CUTANEOUS TOPICAL APPLICATION (SPOT ON), FOR THE TREATMENT AND PREVENTION OF ECTO AND ENDOPARASITOSES AFFECTING DOGS

This application is a 371 application of PCT/US2017/032851 filed May 16, 2017, which claims foreign priority benefit under 35 U.S.C. § 119 of Argentina Application No. 2016-0101448 filed May 18, 2016.

FIELD OF THE PRESENT INVENTION

The present invention pertains to the field of pet animal clinical treatment, and it particularly relates to a monodose integral treatment for the systematic handling of the most frequent parasitoses in dogs. More particularly, the said treatment consists of a cutaneous topical solution for the treatment and prevention of ecto and endoparasitoses via cutaneous topical application.

DESCRIPTION OF THE PREVIOUS ART

External and internal parasitoses are very frequent in dogs, which may be affected anytime in the year and at any age. These parasitoses usually elicit diverse signs that depend on the kind of parasite, degree of infestation and the physiological and immunological condition of the affected animal.

The problem with parasitoses goes beyond the mere suffering of an animal, because under certain circumstances parasites can be transmitted to people, what turns parasitoses into important zoonotic diseases. This is much more frequent in those children who are in close contact with their pets and it is highly related to hygiene, sanitary, environmental and domestic conditions.

The knowledge of parasitic zoonoses, including their clinical manifestations in people and especially children, must be extended to the field of human medicine, the latter permanently cooperating with the veterinary one. On the other hand, pet owners should be informed about the risks parasitic infections pose for health, not only their pets' but also for all of the family members and all of the people living in those pets' environment. Regular deparasitization and health control programs for pets must be clear enough for the public in general, contributing to the set of measures that define responsible ownership of cats and dogs, and play a pivotal role in the caring of public health.

Dog parasitoses constitute a high percentage of the reasons for medical consultation for companion pets and their integral control demands a responsible handling by a veterinary doctor together with the whole society. In order to achieve that goal it is necessary to have tools that be more practical, efficient and safe all the time, so that a parasitic disease may be timely and duly addressed.

Currently there exist a range of commercial products permitting a partial coverage of the spectrum of parasites affecting dogs and, consequently, those products necessarily need to be applied in a combined way, as regards formulations, pharmaceutical forms, routes of administration and duration of treatment. This combination of variables has inevitably triggered an increase of the probability that those treatments not be fulfilled, this resulting in the possibility that those parasites Intended to be fought away develop a resistance as well.

In general, these parasiticide agents are administered orally or parenterally by a veterinary doctor, this being an aspect that adds a difficulty when the time comes for an application.

Skin is an important site for the application of medications, both when local and systemic effects are sought. However, the stratum corneum is the main barrier against the penetration of active ingredients.

The transdermal delivery consists of the administration of therapeutic agents through intact skin, with the purpose of reaching the systemic route and achieving their distribution.

This route of administration provides many advantages with respect to the oral route by allowing, among other things, a controlled administration of a medication. Among those advantages, the ones outstanding are:

It avoids the first pass effect that is created by the metabolism in the liver.

It enables the discontinuation of the administration, thus offering the possibility of reversing any possible undesirable effect rapidly.

It enables an administration in a more controlled and long acting form than the one provided by the oral route.

It enables the alteration of the biological properties of the skin barrier to achieve the absorption.

The systems developed to enhance the penetration (enhancers) mean an important technological challenge capable of increasing the number of drugs available for transdermal administration.

There are chemical and physical methods that enable the enhancement of said penetration, which is known to take place through three routes:

Transdermal penetration through the stratum corneum.

Intercellular penetration through the stratum corneum.

Penetration through hair follicles, sebaceous and sweat glands.

Most molecules penetrate through the skin by the intercellular route and it is because of that that many enhancement techniques are aimed to disorganize or bypass skin architecture.

Penetration enhancers may act through one mechanism, or more, of the following three:

By altering the lipid structure of the stratum corneum.

By interacting with intercellular proteins.

By improving the splitting of the drug, acting as co-enhancers or solvents in the stratum corneum.

The enhancers can also increase the diffusion of the drug through the skin proteins.

Even though medications oriented towards an integral treatment of parasitoses with a single product of topical application can be found commercially, these medications are prescribed for cats and it must be considered that there exist significant physiological differences with respect to dogs that must necessarily be taken into account when a product having equal therapeutic goals has to be developed.

Variations in the behavior of different drugs between both species have been reported, both as regards pharmacokinetic parameters such as absorption, distribution, metabolism and excretion, and as regards the pharmacodynamics of their different active principles (Nerve P. Lefebvre, 2007; Akos, 2012).

Within the aforementioned differences, it becomes particularly important a comparative study on percutaneous penetration performed with Selamectin (macrocyclic lactone, just like Moxidectin), where results of a pharmacology bioavailability of 4% in dogs, with respect to 74% in cats, were obtained (Sarasola, 2002).

The hystological characteristics of the skin barrier of dogs as compared to those of cats explain a large part of this behavior. Variables such as capillary blood flow, density, structure and growth rate of the hair coat, quantity and disposition of sebaceous and sweat glands and, mainly, skin thickness, that is about 21.16±2.55 µm versus 12.97±0.93 µm in dogs and cats respectively (Dermal Absorption and Toxicity Assessment, Second Edition, Roberts, 2008—Animal Skin Morphology and Dermal Absorption, Monteiro-Riviere et al.) considerably influence the absorption of certain drugs and become a challenge when the time comes for the development of a therapeutic formulation adequate and safe for each species.

The patent application AR067751A1 granted to Wyeth Five Giralda Farms provides a composition comprising an effective amount of (a) Praziquantel and (b) a second endoparasiticide agent selected from the group consisting of a macrocyclic lactone, imidacloprid, and a combination of said ingredients; and (c) 4-allyl-2-methoxyphenol as a carrier. Also provided is a method for the treatment of an endoparasitic infection and infestation in a homeothermous animal. As a macrocyclic lactone, Moxidectin can be used. The purpose is to achieve a greater stability and a high concentration of the active ingredients in each application. However, beyond the examples that are given, compositions only having two active ingredients are not effective, in dogs precisely, because dog skin has characteristics of its own that make it very difficult to penetrate.

Therefore, the purpose of the present invention is to enable an integral treatment for dog parasitoses with a single product and in a single, practical and effective application, thus ensuring therapeutic success.

SUMMARY OF THE PRESENT INVENTION

Consequently, is the objective of the present invention a monodose veterinary composition for topical application (spot on) aimed at canines, the said composition comprising:
  (a) Imidacloprid, between 8.18 and 10.00%,
  (b) Moxidectin, between 2.86 and 3.50%,
  (c) Praziquantel, between 8.18 and 10.00%, and
  (d) an aprotic solvent selected from Dimethyl sulphoxide (DMSO), N,N-dimethylacetamide (DMAC), N,N-dimethylformamide (DMF) and their mixtures, between 65.45 and 80.00%;

together with excipients acceptable from the veterinary viewpoint, where the percentages relate to the composition's total weight.

Preferably, the excipients for this composition are Butylhydroxyanisole (BHA), Butylhydroxytoluene (BHT), Thiodipropionic acid, Propyl gallate and Benzyl alcohol.

More preferably, said veterinary composition comprises:
  (a) Imidacloprid, between 8.18 and 10.00%;
  (b) Moxidectin, between 2.86 g and 3.50%;
  (c) Praziquantel, between 8.18 g and 10.00%;
  (d) Dimethyl sulfoxide (DMSO), between 65.45 and y 80.00%;
  (e) Butylhydroxyanisole (BHA), between 0.014 and 0.017%;
  (f) Butylhydroxytoluene (BHT), between 0.006 and 0.008%;
  (g) Thiodipropionic acid, between 0.041 and 0.050%;
  (h) Propyl gallate, between 0.20 g and 0.24 g; and
  (i) Benzyl alcohol, c.s.p. 100.00%

It is another objective of the present invention the use of an effective amount of (a) Imidacloprid, (b) Moxidectin; (c) Praziquantel; and (d) an aprotic solvent selected from Dimethyl sulfoxide (DMSO), N,N-dimethylacetamide (DMAC), N,N-dimethylformamide (DMF) and mixtures of these, together with veterinary acceptable excipients, for the preparation of a monodose veterinary composition for the treatment, control and prevention of ecto and endoparasitoses in canines, where the said veterinary composition is adapted to be administered topically (spot on).

Preferably, the use where said composition is adapted to be applied directly upon the animal's dry skin, poured through immersion, on the nape or back areas.

More preferably, the use where the said ecto or endoparasitic infection is caused by *Ctenocephalides felis, Ctenocephalides canis, Rhipicephalus sanguineus, Ascaris* spp (larva L4, immature adults and adults of *Toxocara canis*), *Ancylostoma* spp, *Uncinaria* spp, *Trichuris vulpis, Dirofilaria immitis* (larva L3 y L4), *Dipylidium caninum, Taenia taenieformis, Otodectes cynotis, Demodex canis, Sarcoptes scabiei* var. *canis*.

DETAILED DESCRIPTION OF THE INVENTION

The present invention consists of a composition of vastly known parasiticide agents in novel combination and concentrations that, by virtue of the election of a suitable and effective carrier, manages to make that all of those agents penetrate by subcutaneous route, thus achieving a hemoconcentration pharmacologically effective hemoconcentration in dogs.

The reference product corresponds to a solution of (a) Imidacloprid, (b) Moxidectin, and (c) Praziquantel; combined with a particular carrier (d) and a multiplicity of veterinary acceptable excipients, to be administered in a topical form (spot on) on canines, for the treatment, control and prevention of ecto and endoparasitoses that affect said animals.

More specifically, the said product is prescribed for the treatment, control and prevention of ecto and endoparasitoses in dogs, caused by:
  Fleas: *Ctenocephalides felis* and *Ctenocephalides canis*.
  Ticks: *Rhipicephalus sanguineus*.
  Nematodes: *Ascaris* spp. (larva L4, immature adults and adults of *Toxocara canis*), *Anquilostomas* spp., *Uncinaria* spp and *Trichuris vulpis*. *Dirofilaria immitis*, larva L3 y L4.
  Cestodes: *Dipylidium caninum, Taenia taenieformis*.
  Mites: *Otodectes cynotis, Demodex canis, Sarcoptes scabiei* var. *canis*.

In a preferred form of practical realization of the veterinary composition according to the present invention, every 100 ml of product comprise:
  (a) Imidacloprid, between 9.00 g and 11.00 g;
  (b) Moxidectin, between 3.15 g and 3.85 g;
  (c) Praziquantel, between 9.00 g and 11.00 g; and
  (d) Dimethyl sulfoxide (DMSO), between 72.00 ml and 80.00 ml;

together with veterinary acceptable excipients.

In a preferred form of practical realization, the composition of the present invention comprises, per each 100 ml of product:
  (a) Imidacloprid, between 9.00 g and 11.00 g;
  (b) Moxidectin, between 3.15 g and 3.85 g;
  (c) Praziquantel, between 9.00 g and 11.00 g; and
  (d) Dimethyl sulfoxide (DMSO), between 72.00 ml and 80.00 ml;
  (e) Butylhydroxyanisole (BHA), between 0.0158 g and 0.0193 g;

(f) Butylhydroxitoluene (BHT), between 0.007 and 0.009 g (g) Thiodipropionic acid, between 0.045 g and 0.055 g;

(h) Propyl gallate, between 0.23 g and 0.28 g; and (i) Benzyl alcohol, c.s.p. 100.00 ml;

where (e), (f), (g), (h) and (i) are the preferred excipients.

By the same token, every 100 g of the product according to the present invention (density=1.10 g/cm$^3$) comprise:

(a) Imidacloprid, between 8.18 g and 10.00 g;

(b) Moxidectin, between 2.86 g and 3.50 g;

(c) Praziquantel, between 8.18 g and 10.00 g; y (c) Dimethyl sulfoxide, between 65.45 g and 80.00 g;

together with veterinary acceptable excipients.

In a preferred way of practical realization of the present invention, every 100 g of product according to the invention (density=1.10 g/cm$^3$) comprise:

(a) Imidacloprid, between 8.18 g and 10.00 g;

(b) Moxidectin, between 2.86 g and 3.50 g;

(c) Praziquantel, between 8.18 g and 10.00 g;

(c) Dimethyl sulfoxide (DMSO), between 65.45 ml and 80.00 ml;

(e) Butylhydroxyanisole (BHA), between 0.014 g and 0.017 g;

(f) Butylhydroxitoluene (BHT), between 0.006 and 0.008 g, (g) Thiodipropionic acid, between 0.041 g and 0.050 g;

(h) Propyl gallate, between 0.20 g and 0.24 g; and (i) Benzyl alcohol, c.s.p. 100.00 g where (e), (f), (g), (h) and (i) are the preferred excipients.

The components (a), (b) and (c) are the active ingredients of the composition; (d), the effective carrier, and (e), (f), (g), (h) and (i), the veterinary acceptable excipients destined to inhibit oxidation and act as vehicles for said components. Thus, the availability of the active ingredients in the conditions and the amounts adequate for a successful integral treatment is ensured.

The aforesaid proportions are based on the pharmacokinetic and pharmacodynamic characteristics of each one of the different components.

Imidacloprid is distributed through the epidermis and the pilosebaceous glands and gets stored in the sebaceous glands, to be gradually released later through the follicular canals.

A study on Beagle dogs to establish the distribution and absorption of the drug when it was administered topically was carried out. To perform the study, Imidacloprid was radioactively marked with $^{14}$C and administered topically in a dose of 12 mg/kg. Subsequently, skin biopsies (5 mm$^2$) were performed on days 3, 7, 15, 21, 29 and 56 after the application.

From the analyses of these skin fragments coming from the lower back of the specimens it was determined that between days 7 and 56, the $^{14}$C-marked imidacloprid was found in high concentrations in the stratum corneum and the sebaceous glands. It was seen that the accumulation of imidacloprid in the fat was taking place because of the drug's migration through the skin and the hairs. No trace of radioactivity was detected in the hypodermis, adipose tissue or the cells of the epidermis basal layer, this revealing that practically there is no absorption of imidacloprid. The prolonged persistence of radioactivity in the cutaneous structures and hairs is in good concordance with the duration of imidacloprid activity after the topical application.

When spray formulations and, mainly, spot—on formulations are used, it is noted that from the place of application there is a translocation of the active ingredient by passive diffusion through the sebaceous secretions present in hairs and skin. This particularity of imidacloprid, independently from the formulation, guarantees its persistence in high concentrations in the hair coat of dogs and cats and, thus, its effectiveness even when the animals get wet or bathed (Harish Chopade, 2010).

It belongs to the chemical group of the neonicotinoids and, according to its pharmacodynamics, its action is similar to acetylcholine's, by exciting nerve cells. Unlike what happens with acetylcholine, that is rapidly broken down by the acetylcholinesterase, imidacloprid is not broken down or this happens very slowly, affecting the nervous system of the parasite insect. This drug is classified within the neonicotinoids because of the ease with which it gets associated with the nicotinic receptors in the postsynaptic cell membrane.

Certain species of insects and mammals have a great proportion of muscarinic receptors, which are less affected by this compound. It is known that in mammals the nicotinic receptor sites are physiologically different from those of insects.

Imidacloprid has a selective activity against fleas and other insect species in a specific way.

Moxidectin is a macrocyclic lactone and its disposition is related to its high lipofilicity characterized by a high volume of distribution, where the drug reservoir is the fatty deposits. Its pharmacokinetics is linear and is influenced by the formulation and the administration route.

Studies performed on humans and canines have shown that the pharmacokinetics is dose-dependent, this resulting into linear increments for plasma concentrations when the doses applied are increased. The plasma spikes are gotten between 3-5 hours and Moxidectin half-life of elimination is species-specific and increases as per the following order: pigs (0.5 days)<dogs (1.8 days)<sheep (2.7 days)<cows (2.8 days). In a 36-day study carried out with dogs of Beagle breed to which Moxidectin was given orally at doses of 0.5 and 2.0 mg/kg/12 hours, it was detected that the concentrations in plasma rose dramatically between days 2 and 8 and remained stables during the 3 following weeks. An increase of four times the original dose resulted in an average increase of more than 8 times the concentrations in plasma.

On the other hand it is known that Moxidectin joints extensively to lipoproteins and albumins, because of which in undernourished animals this may explain the finding of a higher fraction of free drug.

The residues of the drug are detectable for longer periods after the percutaneous administration of Moxidectin, than in the case of oral administration.

Macrocyclic lactones are products of bacterial fermentation that have important parasiticide properties. They are drugs much used in veterinary medicine to control parasites, both internal and external. Multiple therapeutic studies all over the world have shown its wide effectiveness. They cause death by paralysis in various parasite species, since these lactones act as agonists of a subtype of chlorine channels activated by glutamic acid, which are specific for invertebrates. Said channels are absent in higher mammals, although phylogenetically are related to chlorine channels mediated by GABA. It has been shown that at high concentrations, some lactones such as Ivermectin by way of example, can boost the GABA activity upon chlorine channels, causing toxic effects on higher vertebrates.

On the other hand, with the introduction of Ivermectin as an antiparasitic drug it was discovered that some specimens, especially of the Collie breeds, showed a marked neurologic toxicity when they were given the drugs, while other breeds did not, this being a fact that was later related to a defect in P-glycoprotein activity (Manzuc, AVEACA, 2009), a molecule located in the hematoencephalic barrier that limits the entering of the drug into susceptible organs by means of a pumping system towards outside (efflux transporter) that depends on energy (ATP).

Moxidectin belongs to the endectocide group of macrocyclic lactones. It is obtained through a chemical modification of the natural compound Nemadectin, in turn a fermentation product of *Streptomyces cyaneogriseus*, as opposed to Ivermectin, that is a mixture of two closely related compounds. They are powerful insecticide, acaricide and anthelmintic compounds that augment the permeability of membranes to chloride ions, thus leading to paralysis in nematodes and certain classes of ectoparasites. These actions the aforesaid compounds can perform by virtue of their property of joining selectively and with a great affinity, to chloride transport channels related to glutamate, event that takes place in nerve and muscle cells of invertebrates. The outcome of this selective action is the intracellular entry of chlorides and the hyperpolarization of muscle and nerve cells, this resulting in paralysis and death of the parasites. The compounds of this class may also join other chloride transport channels related to other ligands, such as the gamma-aminobutyric acid (GABA) neurotransmitter. The selectivity of their action is because of the fact that mammals do not have glutamate-related channels and the affinity of those compounds for other transport channels is very low, to which must be added a very limited capacity to traverse the hematoencephalic barrier. The studies initially performed on this drug focused on its capability to open $Cl^-$-dependent mimetic GABA channels.

Moxidectin has a powerful activity upon GABA receptors, both in vertebrates and invertebrates, and GABA is known for being a primary inhibitory neurotransmitter in the somatic neuromuscular system of nematodes. However scientists later identified the glutamate-depending $Cl^-$ channels as the main targets of this kind of drugs.

With respect to the other active ingredient, Praziquantel, the quantity of absorbed active ingredient keeps a linear relationship with the dosage, in the same way as Cmx and AUC increase proportionally to the dosage. Plasma peak levels are obtained between 1 hour and three.

It has not been fully elucidated the distribution of Praziquantel in tissue; however, in diverse studies it has been observed the same concentration in tissues and plasma, this concentration being of up to 14-20%.

Praziquantel has a half-life ranging from 0.8 hour to 1.5 hours in adults having normal liver and kidney functions. Metabolites in serum, however, have a half-life ranging from 4 to 5 hours. Although the metabolic pathway is still not known with precision, the drug is rapidly and widely metabolized, in the liver mainly, by means of hydroxylation to monohydroxilated and polyhydroxylated metabolites. It is not known whether these metabolites have an anthelmintic activity.

Praziquantel and its metabolites are excreted through the urine mainly. Between 70 and 80% of an oral dose gets excreted within the first 24 hours, and less than 1% of an oral dose gets excreted with no changes.

As regards its pharmacodynamics, Praziquantel is a synthetic derivative of isoquinoline-pyrazine having activity against several trematode and cestode parasites. In in vivo and in vitro studies it has been discovered that trematodes and cestodes catch Praziquantel very rapidly in a few minutes. This drug causes a tetanic contraction of the parasite musculature and a rapid vacuolization of the parasite's syncytial tegument. This rapid contraction is related to an increase of the membrane permeability to calcium, with a subsequent muscle paralysis. The tegumental vacuolization is restricted to the anterior region of tapeworms strobila, but on the surface of a trematode organism it is more scattered; vacuoles start forming in the syncytial layer, over time their size increases and as a result they create visible blisters on the tegument surface. These blisters explode and produce lesions through which granulocytes, neutrophils and eosinophils enter inside the parasite tissues and cause lysis. Even when it seems to be that the phenomena of muscle contraction and tegument vacuolization depend on calcium, the knowledge of the mode of action of Praziquantel at muscle level is still incomplete.

The net effect is that the parasite comes off its host.

The safety margin of Praziquantel is due to its rapid metabolization and excretion, as well as to its selective effect on susceptible parasites.

The kind of enhancer used has a significant impact on the design and development of the product.

The Dimethyl Sulfoxide (DMSO) is a powerful aprotic solvent. it is colorless, odorless and hygroscopic, and it is used as a universal solvent in many areas of pharmaceutical sciences. The DMSO alone has been used for the topical treatment of inflammation. It works fast as a penetration enhancer and its effects are dependent on its concentration.

There are other enhancer agents chemically similar, such as, for instance, N,N-dimethylacetamide (DMAC) and N,N-dimethylformamide (DMF), that are similar powerful aprotic solvents.

DMAC is an aprotic organic solvent of polar nature vastly used in organic syntheses both at laboratory level and at pharmaceutical level, as well as in the textile industry for synthetic fiber spinning, and for pesticide syntheses. It is a liquid soluble in water, from colorless to yellowish and transparent, and odorless if it is very pure.

DMF is a colorless and odorless liquid that is miscible in water and most organic compounds. DMF is an amidic aprotic solvent used as a solvent for chemical reactions. It is also used as an intracellular cryoprotectant for the cryoconservation of tissues, organs and embryos. Besides it may be used for the manufacture of biodegradable plastics.

Both DMSO, and DMAC and DMF can extract the lipids by making the stratum corneum more permeable by means of aqueous channels. The mechanism of action of the sulfoxides is vastly used. In human skin it has been shown that sulfoxides can denature the intercellular protein, thus modifying the conformation of alpha keratin into the beta form.

By means of the veterinary composition of the present invention, for the first time it has been achieved in dogs the percutaneous penetration of Praziquantel, reaching effective hemoconcentrations for the treatment of cestode-induced parasitoses usually affecting canines. Praziquantel acts directly against *Dipylidium caninum* in the intestinal tract and also, due to its content of Imidacloprid, acts upon the fleas, that are intermediate hosts for these parasites.

On the other hand, the use of Moxidectin in adequate concentrations and dosage has allowed to show, for the first time in dogs, its efficacy for the treatment, control and prevention of *Rhipicephalus sanguineus*, the brown dog tick commonly found in canines. Together with its well-known nematicide action and Imidacloprid's flea-killer contribution, both compounds constitute a novel formulation that through the use of the adequate carrier reach its effectiveness in the animal body with a single and very practical application.

Together with having a fast lethal effect upon the adult forms of ectoparasites, it has a prolonged residual effect capable of keeping dogs flee- and tick-free for up to four weeks.

The veterinary composition of the present invention is an external use product to be directly applied on the skin.

It is presented in single-dose bottles to be applied according to the following scheme:

For dogs weighing up to 4 kilos, a 0.40 milliliter pipette.
For dogs weighing from 5 to 10 kilos, a 1.00 milliliter pipette.
For dogs weighing from 11 to 25 kilos, a 2.50 milliliters pipette.
For dogs weighing from 26 to 40 kilos, a 4.00 milliliters pipette.
For dogs weighing from 41 to 60 kilos, a 6.00 milliliter pipette.

The contents must be directly applied on the dry skin of the animal, in the nape or back region to prevent the animal from licking it. It is important to separate the hairs to obtain an easier application of the product on the skin. The bottle contents must not be downloaded on the hair.

In cases of a high infestation by ticks, it is advisable to apply a drop of product on the skin, on the highest point of the dog's head.

The treatment is carried out with a single dose.

This new way of administration, up to this day neither used nor tested effectively in dogs, brings an ease and a practicality that ensure therapeutic success, since it gets rid of the difficulty posed by an aggressive and biting dog during an oral administration, as well as failures due to vomiting or "fussy dogs that spit out" the pills.

EXAMPLES

Example 1: Manufacturing in Bulk of a Preferred Form of Practical Realization of the Composition of the Present Invention Once performed the control of the supplies it was manufactured a composition of the present invention in bulk, by following the steps hereunder detailed.

To manufacture 100 liters of product it was used a perfectly cleaned vitrified reactor where there were loaded under stirring:

Dimethyl sulfoxide 80.00 dm$^3$
Moxidectin 3.50 kg
Imidacloprid 10.00 kg
Praziquantel 10.00 kg Then stirring was maintained until complete dilution. Once the solids were diluted, and maintaining the stirring, there were added:

BHA 17.50 g
BHT 8.75 g
Thiodipropionic acid 50.00 g
Propyl gallate 250.0 g
Benzyl alcohol c.s.p. 100.00 dm$^3$ Eventually everything was stirred until complete dilution.

Once achieved the complete dilution, a sample was taken and analyzed by HPLC and after a satisfactory result was gotten, the mixture was left to rest for an hour and then a filtration was carried out.

After the filtration the composition obtained is ready to be divided into fractions, in each cannula being included the specified volume for the presentation of the product to be conditioned. Samples for control must be taken out periodically.

Each cannula is tampon printed with the design and the corresponding data, before being placed individually in printed cardboard boxes containing the respective leaflets.

Example 2: Assessment of a Spot-on Veterinary Composition Containing Imidacloprid, Moxidectin and Praziquantel, for the Treatment of Dogs Infested in Natural Conditions with Fleas, Ticks, Nematodes and Cestodes The objective of this study was to assess the effectiveness of a veterinary composition of the present invention (Imidacloprid, Moxidectin and Praziquantel, in pipettes for spot-on application) on the basis of the removal of fleas, ticks; gastrointestinal nematode eggs and proglottids/eggs of cestodes in dogs naturally infested, the assessment, for the case of fleas and ticks, being the removal amount 30 days after treatment, and for the case of internal parasites, 15 days after treatment. The effectiveness against ticks must be set aside because at the time this study was commenced there were no animals infested with said ectoparasites.

For the implementation of this study a complete group of animals was selected and divided into three batches: A, treated, with fleas; B with fleas, untreated control; and C treated, with internal parasites.

Batch A: Groups of treated animals, with fleas. 6 dogs of different breeds naturally infested with fleas were used and a count prior to the application of the product was carried out, with an average minimal parasitization of 10 fleas per animal. The observations were performed at 0 hour, 36 hours, and after 7, 14 and 32 days post treatment (Moment 0).

Batch B: Control group with fleas, untreated: 6 animals with an average minimal parasitization of 10 fleas per animal. Observations performed at 0 hour, 36 hours, and after 7, 14 and 30 days.

Batch C: Group with treated gastrointestinal parasites. 6 half-breed and different breed dogs were used for each parasitic species, in some cases with mixed infestations, naturally infected with *Ascaris* such as *Toxocara canis, Toxocara cati* and *Toxocara leonine; Ancylostoma caninum* and *Unicinaria stenocephal*; and Cestodes: *Dipilidium canino*. Canines were previously selected on the basis of the parasite count and the analyzes of fecal matter, and those animals showing a negative result were rejected.

Data worksheets were made for each animal, containing the animal's profile and the parasites identified in its fecal matter.

Prior to the commencement of the experiment, animals having a positive count of *Ascaris* (*cati, gati* or *leonine*, or all of them at the same time) eggs and animals positive for *Ancylostomas* sp. eggs and animals showing the presence of proglottids or eggs, or both at the same time, of *Dipilidium* sp (in some cases there were mixed infestations) obtained at the moment 0 (feces collection for 3 consecutive days, days −3, −2 and −1 before treatment), the samples being kept in a preservative medium with 10% formalin.

The dogs received the treatment and feces samples were collected from each one of the animals at the moment 1 (days 3, 4 and 5 post treatment). The assessment of the effects of the treatment was performed by means of a macroscopic examination (presence of proglottids, in the case of cestodes and another microscopic examination (eggs, in the case of nematodes) through the flotation and centrifugation of all of the serialized samples (by the Benbrook method), a mild infestation being classified with an X (scarce amount of eggs: from 1 to 2 per microscope field);

a median infestation, with 2× a median infestation (regular amount of eggs: from 3 to 5 per microscope field); and with 3× a severe infestation (abundant amount of eggs: more than 5 per microscope field). The assessment also included the identification of eggs or proglottids or both at the same time.

The number of animals used that had fleas and internal parasites was 6 for fleas, 6 for *Ancylostoma*, 3 for *Toxocara*, 2 for *Trichuris* and 2 for *Dipilidium*.

The age of the canines ranged between 2 months and 9 years, both sexes, having weights ranging between 2 and 20 kg and identified by means of a collar for each animal.

The dogs were kept in individual environments where a recommended comfort (minimal surface 0.7×0.7 m$^2$) had been complied with.

Nourishment was by means of balanced feed premium of a well-known commercial brand and water, all of this on an ad libitum basis.

No other treatments were performed during the study.

The veterinary formula that was tested was Imidacloprid 10.00%; Moxidectin 3.50%; Praziquantel 10.00%; BHA 0.0175 g; BHT 0.00875 g; Dimethyl sulfoxide 80.00 ml; and Benzyl alcohol c.s.p. 100.00 ml.

The dosage range used for each active ingredient was as follows:

Imidacloprid: 10 to 25 mg/kg
Moxidectin: 3.00 to 8.00 mg/kg
Praziquantel: 10.0 to 25 mg/kg The dose employed was as follows:

Dogs between 1 kg and less than 4 kg: a 0.30 ml pipette
Dogs between 4 and 10 kg: a 1.00 ml pipette
Dogs between 11 and 25 kg: a 2.50 ml pipette
Dogs between 25 and 40 kg: a 4.00 ml pipette The veterinary composition of the present invention in a pipette for a spot-on use was applied on the ear base and along the neck, nape and back, by spreading open the hairs and placing the dosing device on the skin.

Method for Counting Fleas and Ticks Existing Upon the Animals

The fleas were counted on each one of the animals included in the different test batches. To carry out the actual counting, the coat hairs were set aside with the fingers and fine-tooth combs that make easier the counting of the *Ctenocephalides* spp were used An individual comb was used for each animal, thus avoiding a casual transfer of the active ingredient among the animals treated and, above all, to those of the untreated control batch.

No assessment of ticks was performed because there were no animals with that ectoparasite.

Once the batches were formed and the commencement of the study decided, the counting was performed on days 0, 36 hours, 7, 21 and 32 days, both upon the treated dog batches and the untreated control dogs.

Method to Count Internal Parasites

A macroscopic examination and a microscopic one by flotation of all of the serialized samples were used.

For the microscopic examination it was used the method of concentration by flotation and centrifugation (with this method most of the eggs in capsule condition, both thick and thin capsules, as well as cysts, oocysts and trophozoites, can be identified).

Benbrook's solution (sugar, 454 g and water, 355 ml), which is made by adding sugar while water is being heated, and 6 ml of formalin are added as preservative for the whole solution; the density is adjusted to 1200-1250 g/cm$^3$.

The following steps were carried out for the examination:

a) The fecal matter was homogenized in the transport flask containing 10% formalin and, at the same time, macroscopic parasite forms were searched for. If the flask had more formalin than fecal matter, before the homogenization a part of the formalin would be thrown away. If, on the other hand, it was seen that there was more fecal matter in relation to the amount of formalin, the sample would be well homogenized and then more 10% formalin would be added.

b) The next step was to filter the fecal matter through a fine-mesh sieve.

c) The portion that was filtered was placed into a conical tube and later centrifuged for 5 minutes at 1500 rpm.

d) The portion left in the sieve was placed under a faucet, where an abundant quantity of water was left to run through it, in order to permit the performance of a microscopic examination in a cleaner and safer way.

e) Once the sample was centrifuged, the centrifuge tubes were removed and the supernatant was discarded and replaced by flotation solution.

f) A new centrifugation was performed for 5 minutes at 1500 rpm.

g) From the surface of the liquid a drop was taken and placed between slide and cover slip to observe through a microscope with magnifications of 10× and 40×.

For fleas: it was used Abbot's formula to compare the infestation at each moment, with control group's, by using the arithmetic mean for each group. Because of a possible contamination resulting from the operator and the low temperatures, Abbot's formula was applied to the results gotten at times 7, 14 and 32 days and then the said results were averaged, a 93.10% of effectiveness having been attained.

Internal parasites: It was determined by the positive or negative results shown at each moment by the samples of fecal matter.

The effectiveness of the product against fleas was assessed macroscopically by the absence/presence of those parasites on a test animal, with the aid of a fine-tooth comb that was passed over diverse regions of the animal. In control animals the process was started in the neck region and as fleas were being counted in the diverse regions, they were placed again on the previously checked neck region of the tested dog.

The effectiveness of the product against internal parasites was macroscopically assessed by the absence/presence of proglottids or parasitary forms and, microscopically, by the amount of eggs in the serialized copro parasitological samples.

Conclusions

Fleas:

The study carried out with the composition of the present invention to show the effectiveness against fleas gave optimal results, both as regards its initial dumping power, ascertained 36 hours post application, and its residual power up to 32 days. From an initial average number of 30 fleas per animal, a number of 0 fleas was achieved in the count 36 hours later and the same held 32 days after the application and for all of the animals, with an effectiveness of 93.10% as per Abbot's formula. It must also be underscored that unlike the untreated control animals, when the fine-tooth comb was passed not only fleas were not found but that 32 days later fecal matter from those parasites was not collected either: in other words, the fine-tooth comb was very clean after each pass.

As regards the animals left as controls, even when the number of fleas diminished after 36 hours, this fact was attributed to two conditions: on the one hand, to some drop of room temperature, but also to the fact that first it was handled the treated group and it is possible that the people that was transporting and restraining them had been contaminated with minimal amounts of the product, what may have had an effect on the control group animals. Devices to heat the rooms and protection panels were then placed and after this, the amount of fleas in the control animals started to increase again, reaching an amount similar to the initial one. After 32 days it was remarkable the amount of flea dirt dragged out by the fine-tooth comb in each pass.

Internal Parasites:

The effectiveness was ascertained on days 7 and 14 post treatment. The effectiveness was ascertained in 7 cases of *Ancylostoma*, 3 of *Toxocara*, 2 of *Trichuris* and 2 of *Dipilidium*, all of the samples being negative on the two days mentioned.

In one of the animals, named Coco, who did not respond to the treatment, the presence of *Hepatozoon canis* was diagnosed, and it was surely this parasite the cause for Coco's low defenses and the lack of action of the product.

Example 3: Assessment of the Effectiveness as a Tickcide of a Formulation for Application Spot-on, Prescribed for the Treatment and Control of Ticks in Canines The suitability and effectiveness of the veterinary composition of the present invention as tickcide, proposed for its utilization as an external antiparasitic drug was assessed, and the product's dumping power, ectoparasite mortality rate and residual power against infestations created by *Riphicephalus sanguineus* in canines (*Canis familiaris*) during 35 days of study were measured.

The study that was performed contemplated the follow-up of the canines for a total period of 35 days.

The experimental unit was composed of a total set of 12 animals divided into two groups identified as Control Group and Treated Group, each one of which had the same number of specimens: 6 canines.

Undefined breed and half-breed canines having homogeneous ages and sizes, both sexes and with a minimal parasite load averaging 15 ectoparasites per animal, were selected. The canines were kept in the premises where the study was to be performed for all the time said study took. They had not been treated previously with the active ingredient of the product nor with any other drug that might have interfered with said product either. Only those specimens who under clinical exploration revealed to be in good health condition were included in the protocol of work. For the discrimination of the participants their nutritional status, corporal condition, mucosal coloration, capillary refill time, cardiac and pulmonary auscultation, abdominal palpation and presence or absence of signs of illness were considered. With no exception at all, those specimens that because of their physiological (pregnancy, suckling, low weight or corporal condition, and the like) or pathological statuses would have compromised or harmed the development of the study, were excluded.

The specimens being assessed were placed in 12 kennels specifically designed for the study. Each kennel was 1.39 m in length, 1.19 m in width, 1.90 m in height, with brick walls, zinc roof and cement floor.

The cleaning of the kennels was performed twice a day by sweeping and mechanical collection of fecal matter and food leftovers. The only washing that was allowed was by tap water.

The feed regime was the same the animals were used to receive and it basically consisted of two daily rations of balanced feed and water ad libitum.

To make up the groups, the canines were designed at random after their amount of initial ectoparasites had been counted.

The specimens were placed in independent kennels, physically separated by a concrete wall and a aisle that was nearly 7 meters long between one group and the next.

The identification of the specimens was carried out through the use of collars having different numbering and color according to the batch, just as the kennels were identified by number and color according to the specimen lodged.

A clinical record was made for each canine, where number and color for the individualization of the animal, number and color of the kennel where it was lodged, group the animal belongs to and a photo for a correct identification were included. Data such as weight, sex, approximate age, coat, distinguishing features, deparatization plan; formulation dosage to be used in the study, its effects and any other remarks that might have been important for the interpretation of the outcomes were collated.

The dosage was assigned on the basis of the following Table 1 according to the weight range of each animal, said dosage having been recorded in the individual worksheet for each animal.

TABLE 1

Weight range as a function of Dosage

| Weight range | Dosage (ml) |
| --- | --- |
| From 1 to 4 kg | 0.30 |
| From 4 to 10 kg | 1.00 |
| From 11 to 25 kg | 2.50 |
| From 25 to 40 kg | 4.00 |

TABLE 2

Administration table according to body weight of the Treated Group

| Specimen | TREATED GROUP Body weight (kg) | Applied milliliters |
| --- | --- | --- |
| CANINE 1 | 7.1 | 1 |
| CANINE 2 | 9.1 | 1 |
| CANINE 3 | 4.2 | 0.3 |
| CANINE 4 | 14.850 | 2.5 |
| CANINE 5 | 23.350 | 2.5 |
| CANINE 6 | 13.8 | 2.5 |

The route of administration was topical (spot-on). The product in spot-on form was placed on the neck region, the application having been done behind the head, at the level of the cervical vertebrae, in the middle of the zone and on the skin, after the hairs were separated in such a way that there were no noticeable spills on the coat.

The Treated Group ended up made up of 6 (six) animals naturally infested with a minimum of 15 (fifteen) ticks per animal at the start of the study. For the counting of parasites, each animal was manually examined by a trained worker exclusively assigned to the control and count of said parasites.

The 6 remaining specimens, in similar conditions, were used as Control Group.

Each animal was counted on the day 0, when the product was applied, and then 24 and 48 hours later, to continue on days 7, 14, 21, 28 and 35 post treatment as from day 0. To assess the persistence of the effectiveness, each animal was re-infested in a natural way.

The result obtained for each dog in each one of the counts performed along the study up to day 35 post treatment, is shown in Table 3.

To assess the percentage of effectiveness E it was used Abbot's formula, the results of which are detailed in Table 4.

$$E(\%)=100\times(A-B)/A$$

A=Geometric mean of the number of parasites in the control group

B=Geometric mean of the number of parasites in the treated group with no incidents to report. The animal 7 did not receive the treatment because it was a negative control.

Samples were taken after 1, 2, 4, 6, 12, 24 and 48 hours with no incidents to report. In a period not longer than 2 hours, all of the samples were sent to the Laboratory, where they were centrifuged, and their plasma separated and frozen to −20° C. until the samples were quantified.

The following table expresses the individual values of plasma concentrations of Praziquantel obtained.

TABLE 3

Count of Riphicephalus spp. on days 0, 1, 2, 7, 14, 21, 28 and 35 days post treatment

|  | DAY 0 | DAY 1 | DAY 2 | DAY 7 | DAY 14 | DAY 21 | DAY 28 | DAY 35 |
|---|---|---|---|---|---|---|---|---|
| TREATED GROUP | | | | | | | | |
| CANINE 1 | 30 | 20 | 10 | 3 | 4 | 2 | 7 | 11 |
| CANINE2 | 18 | 8 | 7 | 3 | 0 | 5 | 4 | 9 |
| CANINE 3 | 24 | 10 | 6 | 2 | 1 | 0 | 15 | 21 |
| CANINE 4 | 50 | 43 | 25 | 10 | 3 | 0 | 0 | 4 |
| CANINE 5 | 19 | 18 | 9 | 4 | 1 | 0 | 8 | 14 |
| CANINE 6 | 50 | 50 | 26 | 7 | 0 | 0 | 6 | 13 |
| AVERAGE | 31.83333 | 24.833333 | 13.833333 | 4.8333333 | 1.5 | 1.1666667 | 6.6666667 | 12 |
| CONTROL GROUP | | | | | | | | |
| CANINE 1 | 16 | 31 | 45 | 25 | 33 | 46 | 50 | 50 |
| CANINE2 | 35 | 38 | 50 | 28 | 40 | 32 | 50 | 50 |
| CANINE 3 | 34 | 37 | 24 | 3 | 6 | 17 | 24 | 46 |
| CANINE 4 | 21 | 22 | 30 | 12 | 25 | 34 | 41 | 50 |
| CANINE 5 | 37 | 28 | 27 | 12 | 21 | 50 | 50 | 50 |
| CANINE 6 | 21 | 22 | 42 | 24 | 43 | 50 | 50 | 50 |
| AVERAGE | 27.333333 | 29.666667 | 36.333333 | 17.333333 | 28 | 38.166667 | 44.166667 | 49.333333 |

TABLE 4

Percentage of Efectiveness (PE)

| | Days post treatment | | | | | | | |
|---|---|---|---|---|---|---|---|---|
|  | DAY 0 | DAY 1 | DAY 2 | DAY 7 | DAY 14 | DAY 21 | DAY 28 | DAY 35 |
| CONTROL GROUP | 24.166667 | 25.833333 | 39.166667 | 20.666667 | 35.5 | 44.083333 | 47.083333 | 49.666667 |
| TREATED GROUP | 25.75 | 27.75 | 37.75 | 19 | 31.75 | 41.125 | 45.625 | 49.5 |
| % of EFFECTIVENESS (PE) | N/D | 16.29 | 61.92 | 72.11 | 94.64 | 96.94 | 84.9 | 75.67 |

Conclusions

From Table 4 it is understood that the highest percentage of effectiveness is reached 21 days after the administration, when it amounts to 96.94%.

The dumping power of the product assessed was greater than 50% 48 hours after the application of the product, with an effectiveness, on day 2, of 61.92%.

From the analysis of Table 4 it emerges that the effectiveness of the product regarding the *Riphisephalus* spp. parasitosis in a canine species exceeded 75% on day 14, to remain above that range in all of the subsequent counts.

Example 4: Pharmacokynetics of Praziquantel Administered by Means of the Spot-on Technique on Adult Dogs 6 canines received Praziquantel in doses of 0.145 ml/kg in a composition of the present invention by a spot-on route,

TABLE 5

Plasma concentrations of Praziquantel measured in adult dogs treated with Praziquantel by a spot-on route

| Time (hs) | Dog 1 | Dog 2 | Dog 3 | Dog 4 | Dog 5 | Dog 6 | Dog 7* |
|---|---|---|---|---|---|---|---|
| 0 | 0.0 | 0.0 | 0.0 | 0.0 | 0.0 | 0.0 | 0.0 |
| 1 | 33.6 | 18.3 | 47.7 | 12.6 | 22.8 | 28.8 | 0.0 |
| 2 | 48.9 | 29.4 | 58.4 | 14.1 | 30.9 | 38.1 | 0.0 |
| 4 | 77.6 | 42.7 | 68.1 | 31.0 | 52.8 | 48.8 | 0.0 |
| 6 | 63.7 | 43.9 | 57.8 | 38.6 | 59.0 | 40.3 | 0.0 |
| 12 | 42.4 | 30.5 | 35.1 | 36.4 | 45.1 | 19.8 | 0.0 |
| 24 | 20.2 | 9.4 | 13.1 | 18.5 | 9.1 | 6.0 | 0.0 |
| 48 | 7.0 | 0.0 | 6.7 | 6.7 | 2.5 | 3.2 | 0.0 |

Plasma concentrations are given in ng/ml.

*Dog 7 did not receive treatment, consequently becoming the negative control of the study.

TABLE 6

Pharmacokinetic parameters for adult dogs treated with
Praziquantel by a spot-on route

| Dog | AUC/inf | CMAX | TMAX |
|---|---|---|---|
| 1 | 1321.30 | 77.6 | 4 |
| 2 | 731.9 | 43.9 | 6 |
| 3 | 1090.58 | 68.1 | 4 |
| 4 | 990.89 | 38.6 | 6 |
| 5 | 1002.15 | 59 | 6 |
| 6 | 626.59 | 48.8 | 4 |
| Median: | 996.52 | 53.9 | 5 |
| Max: | 1321.30915 | 77.6 | 6 |
| Min: | 626.596885 | 38.6 | 4 |

Conclusions:

The present study is the first one to furnish pharmacokinetic data of a Praziquantel spot-on formulation to be administered to dogs. The results show a Tmax of 5 hours with a range going from 4 to 6 hours and the existence of plasma concentrations detectable up to 48 hours, with a Cmax of 77.6 ng/ml for an administered dose of 14.5 mg/kg.

Praziquantel has been formulated for its spot-on administration in products intended for the treatment of cats. For example, commercially there exists the product Profender® formulated in association with two other antiparasitics. According to the report on Profender® approved by the European Medicines Agency (EMA), the maximal concentration of a Praziquantel dose similar to the one administered in this study (0.14 ml/kg) was 61.3±44.1 ng/ml, what is coincident with the data shown (EMA, 2008). On the other hand, the Tmax for Praziquantel recorded in the present study is higher than the one reported in the Summary issued by the Commitee of Veterinary Medicinal Products for Praziquantel administered in oral form to dogs, a peak being reached between 30 and 120 minutes (EMEA—European Medicines Evaluation Agency, 1996, Praziquantel: Summary Report (1). Obtained from: http://www.ema.europa.euldocs/en GB/document_library/Maximum Residue_Limits_Report|2009111|WC500015784.pdf).

Xie et al. (Xie, S., Pan, B., Shi, B., Zhang, Z., Zhang, X., Wang, M., & Zhou, W. (2011). Solid lipid nanoparticle suspension enhanced the therapeutic efficacy of praziquantel against tapeworm. *International Journal of Nanomedicine*, 6, 2367-2374. doi:10.2147/IJN.S24919) compared the pharmacokinetic parameters of a Praziquantel native formulation to a nanoparticulated one, both of them for subcutaneous administration. The dose administered in this case was 5 mg/kg, that is to say a bit more than three times smaller than the one used in our study. Xie et al. study showed a Cmax of 47.82 ng/ml, with a Tmax of 1.45 hour and values below 10 ng/ml after 48 hours. Therefore, it can be concluded that the Cp ranges found in this study may be compatible with records published by other authors. The higher rate of absorption guaranteed by the subcutaneous route, as reported by Xie et al. might be compensated by the greater ease of administration provided by the spot-on route. It should be noted that after 48 hours, plasma concentrations detected by one of the formulations and the other are comparable.

Summarizing: the veterinary composition as per the present invention, that contains Praziquantel to be administered by a spot-on route to dogs, exhibits a pharmacokinetic behavior comparable to the one reported for similar formulations applied through other administration routes.

What is claimed is:

1. A monodose veterinary composition consisting of:
 (a) imidacloprid at a concentration of between 8.18 and 10.00%;
 (b) moxidectin at a concentration of between 2.86 and 3.50%;
 (c) praziquantel at a concentration of between 8.18 and 10.00%;
 (d) dimethyl sulfoxide (DMSO), N,N-dimethylacetamide (DMAC), N,N-dimethylformamide (DMF), or mixtures thereof at a concentration of between 65.45 and 80.00%; and
 (e) one or more excipients acceptable from a veterinary viewpoint, wherein:
 each of the recited percentages is relative to the total weight of the monodose veterinary composition; and
 the monodose veterinary composition is adapted for application to a canine.

2. The monodose veterinary composition according to claim 1, wherein the one or more excipients comprises butylhydroxyanisole (BHA), butylhydroxytoluene (BHT), thiodipropionic acid, propyl gallate, or benzyl alcohol.

3. The monodose veterinary composition according to claim 1, wherein:
 the dimethyl sulfoxide (DMSO) is present at a concentration of between 65.45 and 80.00%; and
 the one or more excipients comprise:
 butylhydroxyanisole (BHA) at a concentration between 0.014 and 0.017%;
 butylhydroxytoluene (BHT) at a concentration between 0.006 and 0.008%;
 thiodipropionic acid at a concentration between 0.041 and 0.050%;
 propyl gallate at a concentration between 0.20 and 0.24%; and
 benzyl alcohol, c.s.p. 100.00; and
 each of the recited percentages is relative to the total weight of the monodose veterinary composition.

4. A method for treating an ectoparasite infection or an endoparasite infection comprising administering the monodose veterinary composition according to claim 1 topically (spot on) to a canine.

5. The method according to claim 4, wherein the monodose veterinary composition is administered directly to the canine's skin, administered by immersion, administered to the canine's nape, or administered to the canine's back.

6. The method according to claim 5, wherein:
 the ectoparasite infection is caused by an organism of the species *Ctenocephalides felis*, an organism of the species *Ctenocephalides canis*, or an organism of the species *Rhipicephalus sanquineus*; or
 the endoparasite infection is caused by an organism of the species *Ascaris* spp., a larva of the species *Toxocara canis*, an immature adult of the species *Toxocara canis*, an adults of the species *Toxocara canis*, an organism of the species *Ancylostomas* spp., an organism of the species *Uncinaria* spp., an organism of the species *Trichuris vulpis*, a larva L3 of the species *Dirofilaria immitis*, a larva L4 of the species *Dirofilaria immitis*, an organism of the species *Dipylidium caninum*, an organism of the species *Taenia taenieformis*, an organism of the species *Otodectes cynotis*, an organism of the species *Demodex canis*, or an organism of the species *Sarcoptes scabiei* var. *canis*.

* * * * *